United States Patent
Christy et al.

(10) Patent No.: US 8,204,689 B2
(45) Date of Patent: Jun. 19, 2012

(54) MOBILE SOIL MAPPING SYSTEM FOR COLLECTING SOIL REFLECTANCE MEASUREMENTS

(75) Inventors: Colin Christy, Salina, KS (US); Paul Drummond, Minneapolis, KS (US)

(73) Assignee: Veris Technologies, Inc., Salina, KS (US)

( * ) Notice: Subject to any disclaimer, the term of this patent is extended or adjusted under 35 U.S.C. 154(b) by 828 days.

(21) Appl. No.: 12/253,594

(22) Filed: Oct. 17, 2008

(65) Prior Publication Data

US 2009/0112475 A1    Apr. 30, 2009

Related U.S. Application Data

(60) Provisional application No. 60/982,395, filed on Oct. 24, 2007.

(51) Int. Cl.
  *G01V 3/38*  (2006.01)
  *G01N 31/00*  (2006.01)
(52) U.S. Cl. .............................................. 702/5; 702/28
(58) Field of Classification Search .................. 702/5, 28
  See application file for complete search history.

(56) References Cited

U.S. PATENT DOCUMENTS

| | | | |
|---|---|---|---|
| 4,992,657 A | 2/1991 | Reisner | |
| 5,038,040 A * | 8/1991 | Funk et al. | 250/339.02 |
| 5,044,756 A | 9/1991 | Gaultney et al. | |
| 5,128,882 A | 7/1992 | Cooper et al. | |
| 5,461,229 A | 10/1995 | Sauter et al. | |
| 5,548,115 A | 8/1996 | Ballard et al. | |
| 5,739,536 A | 4/1998 | Bucholtz et al. | |
| 5,882,101 A * | 3/1999 | Chao | 351/47 |
| 6,608,672 B1 | 8/2003 | Shibusawa et al. | |
| 6,753,966 B2 | 6/2004 | Von Rosenberg | |
| 6,853,937 B2 | 2/2005 | Shibusawa et al. | |
| 6,937,939 B1 | 8/2005 | Shibusawa et al. | |
| 7,216,555 B2 | 5/2007 | Drummond et al. | |
| 7,245,373 B2 * | 7/2007 | Soller et al. | 356/325 |
| 2002/0039186 A1 * | 4/2002 | Rosenberg | 356/432 |
| 2005/0172733 A1 * | 8/2005 | Drummond et al. | 73/864.41 |
| 2006/0017923 A1 * | 1/2006 | Ruchti et al. | 356/326 |
| 2011/0106451 A1 * | 5/2011 | Christy et al. | 702/5 |

* cited by examiner

*Primary Examiner* — Michael Nghiem
(74) *Attorney, Agent, or Firm* — Jeffrey L. Thompson; Thompson & Thompson, P.A.

(57) ABSTRACT

A mobile soil mapping system includes an implement for traversing a field to be mapped, and a reflectance module carried by the implement for collecting spectroscopic measurements of soil in the field. The reflectance module has a light source, an optical receiver for transmitting light to a spectrometer, and a shutter system that alters the optical path between the light source and the optical receiver. The shutter system allows the system to automatically collect a dark reference measurement and a known reference material measurement at timed intervals to compensate for drift of the spectrometer and the light source. A self-cleaning window on the reflectance module has a lower surface maintained in firm contact with the soil during operation. External reference blocks are used to calibrate the system to ensure standardized, repeatable data. Additional sensors are carried by the implement to collect other soil data, such as electrical conductivity and temperature.

23 Claims, 10 Drawing Sheets

MOBILE SOIL MAPPING SYSTEM FOR COLLECTING SOIL REFLECTANCE MEASUREMENTS

RELATED APPLICATIONS

This application claims priority of U.S. Provisional Application No. 60/982,395 filed on Oct. 24, 2007. The content of this prior application is incorporated herein by reference.

BACKGROUND OF THE INVENTION

1. Field of the Invention

The present invention relates generally to methods and devices for analyzing and mapping soil properties within a field. In particular, the present invention relates to methods and devices for collecting and standardizing soil reflectance data.

2. Description of the Related Art

Accurately and affordably mapping soil properties within a field has proven challenging for soil scientists and precision agriculture practitioners. The sampling density needed to capture small spatial scale variability is impractical using conventional sampling and analysis methods. One of the challenges soon to be facing agricultural soil measurements involves accurately identifying soil carbon sequestration levels. This arises out of the need to reduce atmospheric carbon by increasing the amount of carbon stored in the soil. This would involve contracting with growers to sequester carbon in their soils, and would require accurate measurements to verify the amount of carbon stored. What makes measuring changes in soil carbon levels challenging is the expected carbon increase is small relative to the amount of carbon variability within the field. A device that can map soil carbon variability, used in conjunction with a small number of lab-analyzed soil samples, will lead to improved accuracy of carbon maps.

Soil measurements using diffuse near-infrared spectroscopy (NIR) have been shown to relate closely to soil carbon levels. Reflectance in the NIR portion of the electromagnetic spectrum is highly influenced by molecules containing strong bonds between relatively light atoms. These bonds tend to absorb energy at overtones and combinations of the mid infrared fundamental vibration frequencies. The predominant absorbers in the NIR region are the C—H, N—H, and O—H functional groups, making the NIR region ideal for quantifying forms of carbon, nitrogen and water, respectively. In addition, NIR measurements can frequently be related to other properties of interest, including soil pH, calcium and magnesium.

In order to collect reliable field measurements of soil NIR, the device needs to include internal and external calibration mechanisms that insure calibrated measurements. Soil must be presented to the spectrometer with minimal interference from ambient light, dust, mud, or plant residue. Finally, due to the inherently complex nature of spectroscopy, the method of processing on-the-go soil NIR measurements must be incorporated into a system that performs several critical functions.

Shibusawa U.S. Pat. Nos. 6,608,672 and 6,853,937 both claim the excavation of a survey chamber—a cavity in the soil under the window. This may work acceptably at slow speeds in tilled, well-mixed soil of medium texture and moisture, but it's doubtful that it could be effective in a commercial agricultural application, where conditions and speeds are more challenging.

Shibusawa U.S. Pat. No. 6,853,937 also discloses an EC sensor attached to the excavating shoe. However, Shibusawa's EC sensor only provides a single depth of investigation, at the depth of NIR data collection.

SUMMARY OF THE INVENTION

A mobile soil mapping system includes an implement for traversing a field to be mapped, and a reflectance module carried by the implement for collecting spectroscopic measurements of soil in the field. The reflectance module has a light source, an optical receiver for transmitting light to a spectrometer, and a shutter system that alters the optical path between the light source and the optical receiver. The shutter system allows the system to automatically collect a dark reference measurement and a known reference material measurement at timed intervals to compensate for drift of the spectrometer and the light source. A self-cleaning window on the reflectance module has a lower surface maintained in firm contact with the soil during operation. External reference blocks are used to calibrate the system to ensure standardized, repeatable data. Additional sensors are carried by the implement to collect other soil data, such as electrical conductivity and temperature.

According to one aspect of the present invention, a soil mapping system is provided, comprising: an implement for traversing a field to be mapped; and a reflectance module carried by the implement for collecting spectroscopic measurements of soil in the field, the reflectance module having a light source, an optical receiver for transmitting light to a spectrometer, and a shutter system for altering an optical path between the light source and the optical receiver. The shutter system has a first position that blocks reflected light from the light source from reaching the optical receiver to provide a dark reference measurement, a second position that allows light from the light source to illuminate and reflect off a known reference material to provide a reference material measurement, and a third position that allows light to illuminate and reflect off the soil to provide soil data measurement.

According to another aspect of the present invention, a soil mapping system is provided, comprising: an implement for traversing a field to be mapped; and a reflectance module carried by the implement for collecting spectroscopic measurements of soil in the field, the reflectance module having a light source, an optical receiver for transmitting light to a spectrometer, and a window located between the light source and the soil being measured. The window has a lower surface arranged to maintain firm contact with the soil during operation to prevent dust, mud and ambient light from interfering with the spectroscopic measurements.

According to another aspect of the present invention, a soil mapping system is provided, comprising: an implement for traversing a field to be mapped; a reflectance module carried by the implement for collecting spectroscopic measurements of soil in the field; and a first external reference module for providing a first external reference material measurement for calibrating the system. The first external reference module comprises a means for aligning and temporarily securing the reference module to the reflectance module, and a first known reference material aligned with a measurement window on the bottom of the reflectance module.

According to another aspect of the present invention, a soil mapping system is provided, comprising: an implement for traversing a field to be mapped; a reflectance module carried by the implement for collecting spectroscopic measurements of soil in the field; first and second electrical conductivity measurement devices carried by the implement for collecting electrical conductivity measurements of the soil in the field at two different depths; and a soil temperature measuring device for collecting soil temperature data from the soil in the field.

According to another aspect of the present invention, a method of collecting standardized soil reflectance data is provided, comprising: providing an implement for traversing a field to be mapped and a reflectance module carried by the implement for collecting spectroscopic measurements of soil in the field, the reflectance module having a light source and an optical receiver for transmitting light to a mobile spectrometer; collecting a dark reference measurement and a known internal reference material measurement within the reflectance module periodically as the implement is being used; and using the dark reference measurement and known internal reference material measurement to compensate for drift in the mobile spectrometer and light source during use.

Numerous other objects of the present invention will be apparent to those skilled in this art from the following description wherein there is shown and described an embodiment of the present invention, simply by way of illustration of one of the modes best suited to carry out the invention. As will be realized, the invention is capable of other different embodiments, and its several details are capable of modification in various obvious aspects without departing from the invention. Accordingly, the drawings and description should be regarded as illustrative in nature and not restrictive.

BRIEF DESCRIPTION OF THE DRAWINGS

The present invention will become more clearly appreciated as the disclosure of the present invention is made with reference to the accompanying drawings. In the drawings.

DETAILED DESCRIPTION OF THE INVENTION

Figure 1:
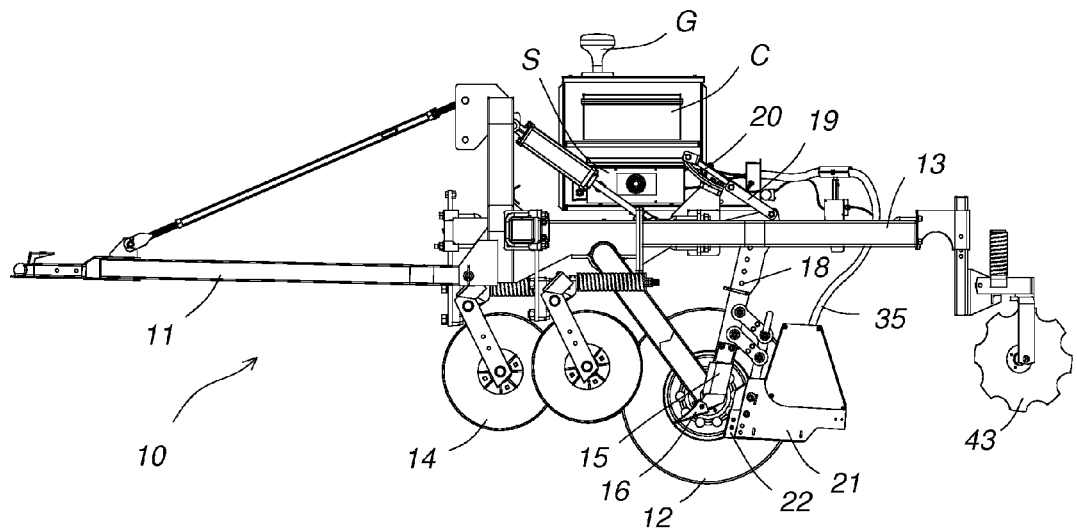
FIG. 1 is an elevation view of a soil mapping system according to the present invention.

A mobile soil mapping system for collecting on-the-go reflectance measurements of soil in a field according to the present invention will now be described in detail with reference to FIGS. 1 to 16 of the accompanying drawings.

The soil mapping system is used to measure diffuse reflectance of soil at sampled locations while traveling through the field. The system includes an implement 10 for traversing a field to be mapped, a GPS receiver G to geo-reference all data collected, a portable computer C to process and record data, a spectrometer S to measure diffuse light reflectance, and various other components mounted on and carried by the implement. The implement 10 includes a draw bar 11 for connecting to a towing vehicle, a set of support wheels 12 that can be vertically adjusted to raise and lower the implement relative to the soil, and a frame 13 on which the various other components are mounted.

A fluted coulter 14 is connected to the implement 10 near the front of the frame 13. The coulter 14 functions to cut through crop residue and open a narrow slit in the soil. A shank assembly 15 containing a ripping tooth 16 follows behind the coulter 14 and further opens the slit into a soil slot 17. The operating depth of the shank assembly 15 is adjustable using a series of adjustment holes 18 that adjust the vertical position of the shank assembly 15 relative to the frame 13. The shank assembly 15 has a trip mechanism 19, which provides protection against damage from rocks and other obstacles. The trip mechanism 19 is a toggle-trip design, which means in order to activate, the pressure against the shank assembly 15 must reach an adequate force to overcome the resistance provided by a stack of three leaf-springs 20. The shank assembly 15 is removable, which may be desirable for operation in extremely high residue situations.

Figure 2:
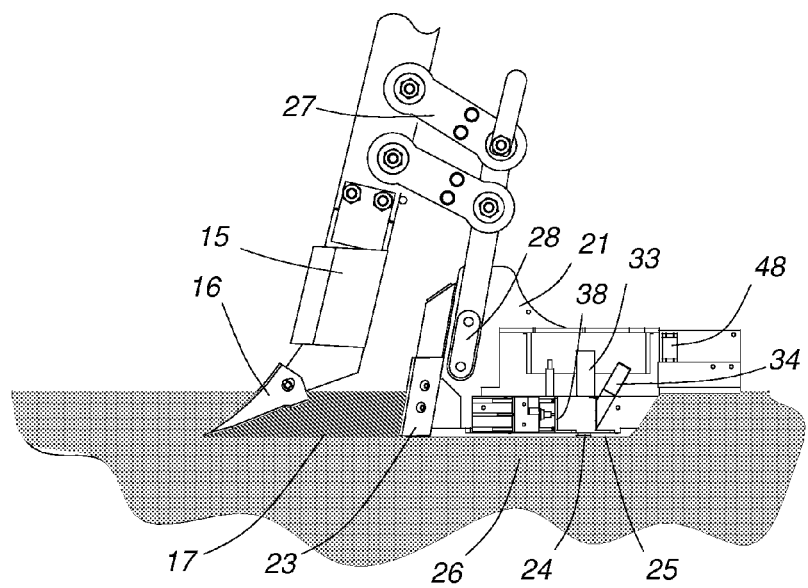
FIG. 2 is an elevation view of a shank assembly and reflectance module of the soil mapping system, as they pass through soil during operation.
Figure 3:
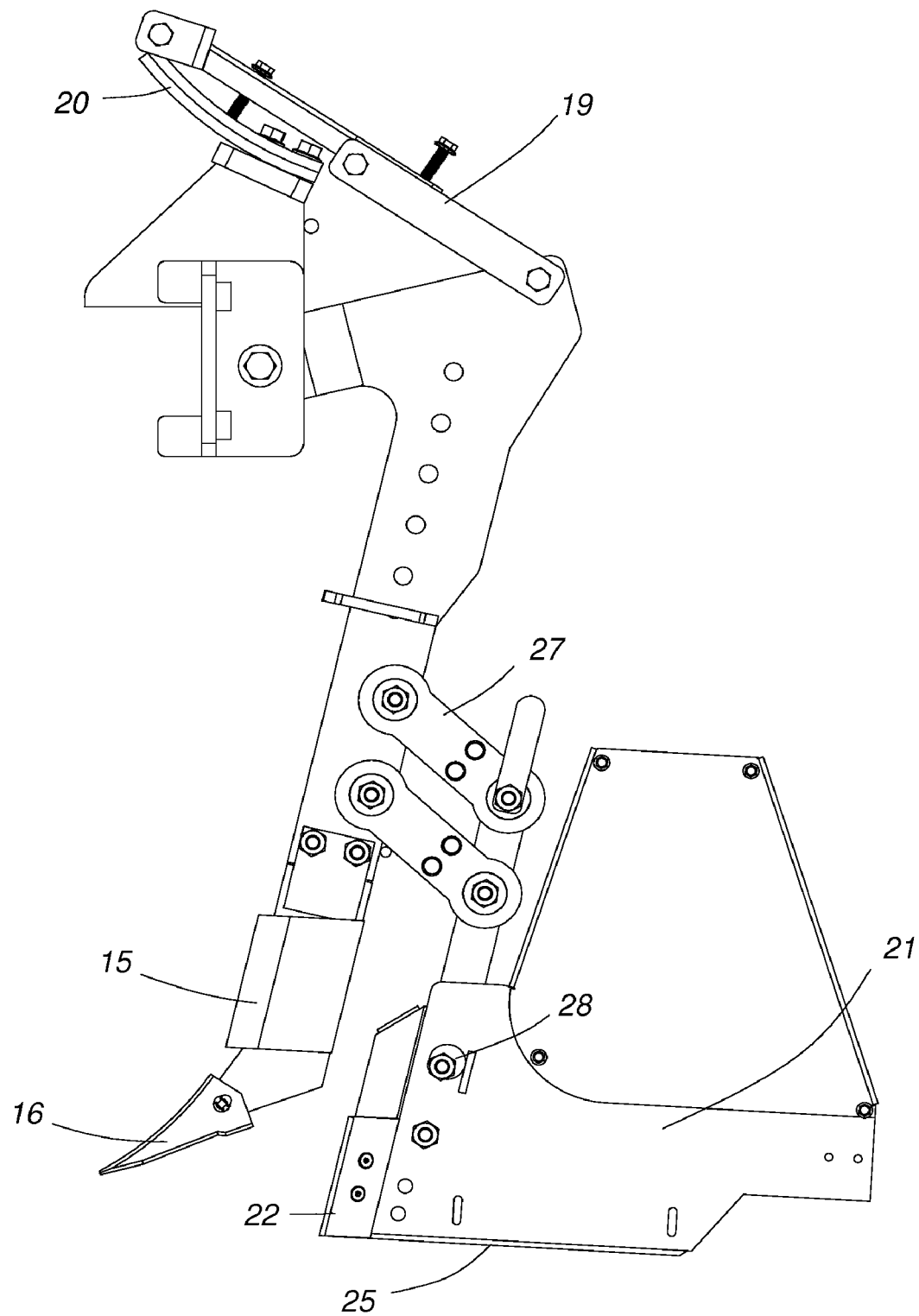
FIG. 3 is a detail elevation view of the shank assembly and reflectance module.
Figure 4:
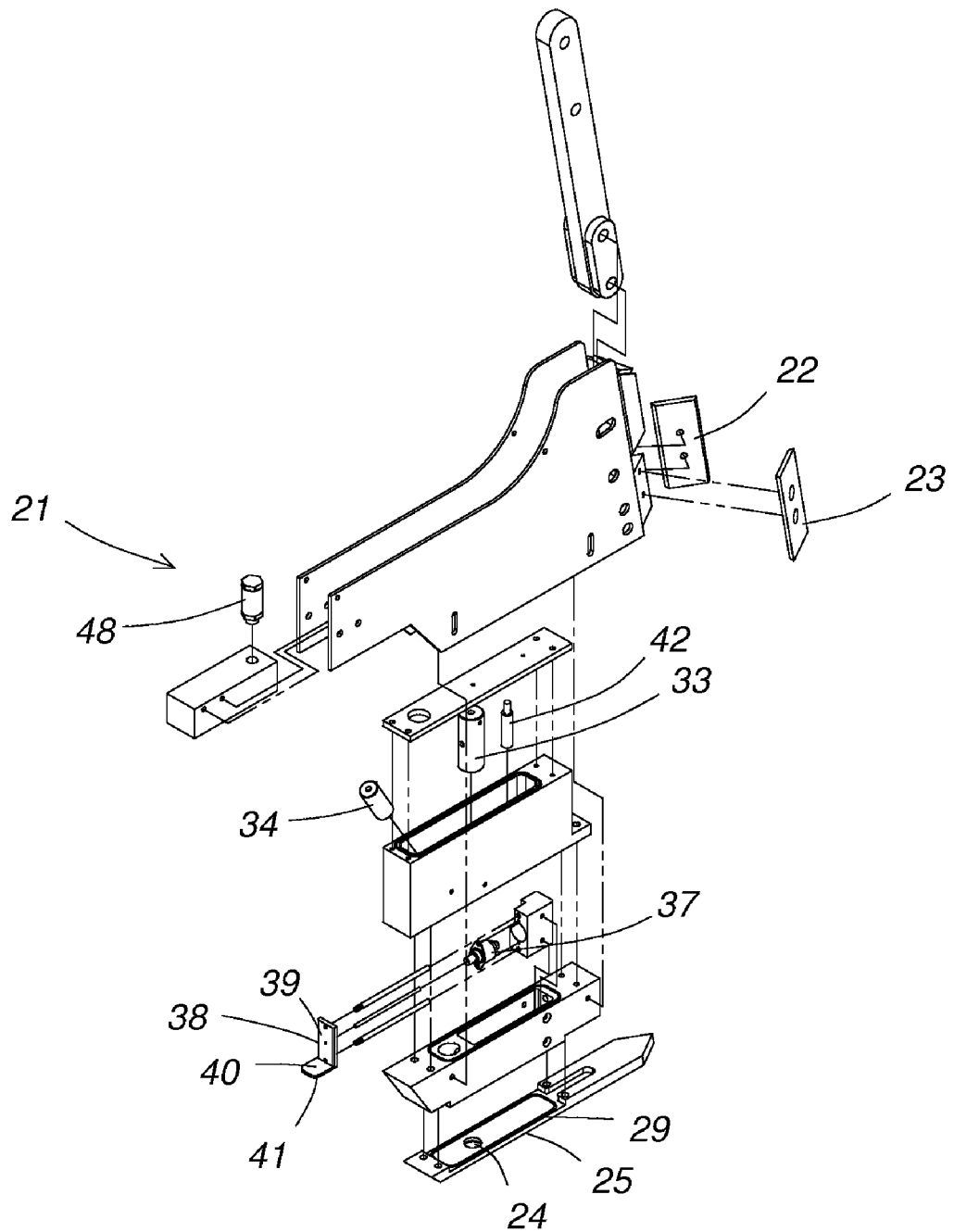
FIG. 4 is an exploded perspective view of the reflectance module showing the various components thereof.

A reflectance module 21 attaches directly behind the shank assembly 15 and is a critical component for collecting high quality spectroscopic measurements. There are two wear plates 22, 23 on the front of the reflectance module 21 that can be rotated 180° to extend wear life. A sapphire window 24 is provided in a wear plate 25 on the bottom side of the reflectance module 21. As shown in FIG. 2, the window 24 is arranged to maintain firm contact with the soil 26 to prevent dust, mud, and ambient light from interfering with the spectroscopic measurements. By not allowing any space between the window 24 and the soil 26, there is no dust billowing up in front of the window 24, and any wet soil that might adhere to the window 24 is cleaned off by the pressure of the window 24 against the bottom of the soil slot 17. Also, because the window 24 is pressed flat against the slot 17, no ambient light can enter the view of the optical components inside the reflectance module 21.

In order for the sapphire window 24 on the bottom side of the reflectance module 21 to maintain firm contact with the soil 26, the position of the reflectance module 21 relative to the soil is important. The reflectance module 21 mounts to the shank assembly 15 with a parallel linkage 27, which allows the reflectance module 21 to follow undulations in terrain and still maintain its proper orientation to the soil during the full range of vertical movement. A spring arrangement (not shown) can be used with the parallel linkage 27, if necessary, to increase the down pressure applied to the reflectance module 21. A cam adjustment 28 allows the pitch of the reflectance module 21 to be adjusted relative to the shank assembly 15, further ensuring adequate soil contact.

The wear plate 25 in which the window 24 is mounted is a replaceable component and has an o-ring seal 29 to keep the internal components of the reflectance module 21 free of soil and moisture. The wear plate 25 has four small recesses 30 that align with pins 31 on a set of external reference blocks 32 (further described below), allowing an external reference material to be quickly placed directly in front of the window 24 for easy and accurate reference calibrations.

Inside the reflectance module 21 are machined cavities holding the tungsten halogen bulb 33 used to illuminate the soil 26, and the optical receiver lens 34 to direct reflected light into a fiber optic 35 for transmission to the spectrometer S. The light source 33 and optical receiver 34 can be similar to those disclosed in the prior art for collecting soil reflectance data.

The light source 33 and spectrometer S associated with the optical receiver 34 have a tendency to drift over time during use, which can lead to skewed data. To compensate, the system needs to collect a known reference measurement and a dark measurement periodically, so that these measurements can be used to transform the data as necessary. Although a dark measurement could be taken by shutting off the light source 33, this has a tendency to shorten the bulb life and may even increase the drift of the light source over time. On the other hand, a known reference measurement could be taken by placing a known external reference material against the outer surface of the window 24 of the reflectance module 21. However, this requires user interaction that would tend to slow the data collection process and would be impractical in many commercial settings.

Figure 5:
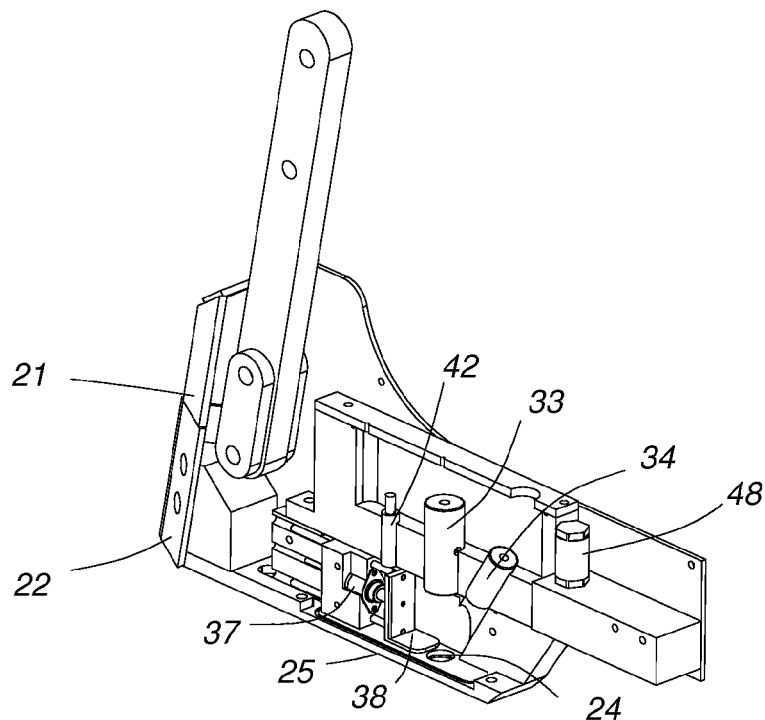
FIG. 5 is a cutaway perspective view of the reflectance module with a shutter element in an open position for collecting external reflectance data.
Figure 6:
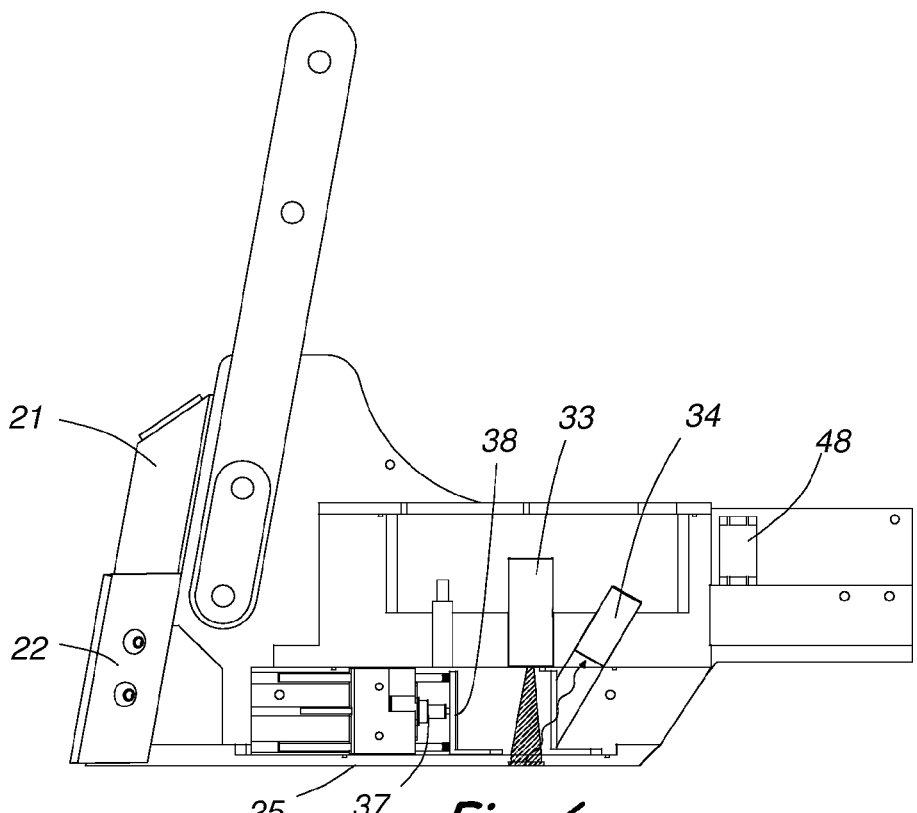
FIG. 6 is a cutaway elevation view of the reflectance module with the shutter element in its open position for collecting external reflectance data.

Accordingly, the Applicants have developed a system that allows both a dark measurement and a known material measurement to be collected periodically and automatically without shutting off the light source 33. This is accomplished using a single actuator 37 that moves a shutter 38 from an open position, as shown in FIGS. 5 and 6, for collecting external reflectance data, into two other positions for collecting dark and reference measurements.

Figure 7:
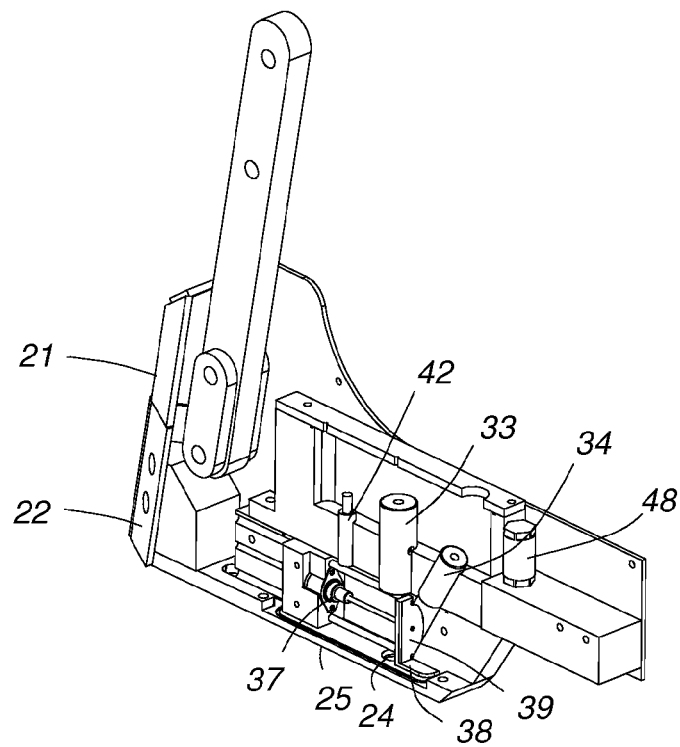
FIG. 7 is a cutaway perspective view of the reflectance module with the shutter element in a fully closed position for collecting a dark spectroscopic measurement.
Figure 8:
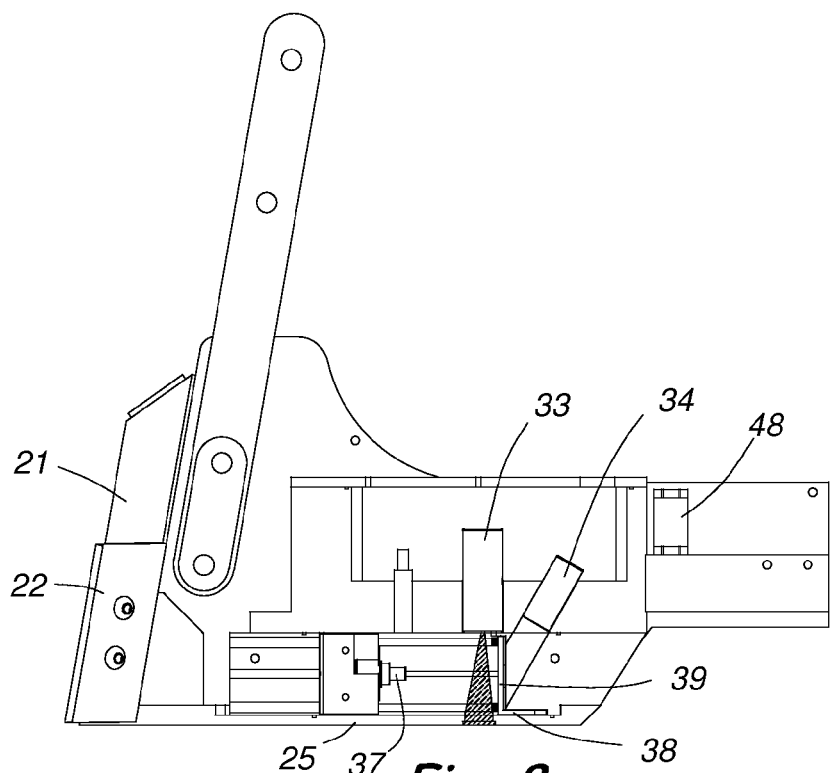
FIG. 8 is a cutaway elevation view of the reflectance module with the shutter element in its fully closed position for collecting a dark spectroscopic measurement.

The dark measurement position of the shutter 38 is shown in FIGS. 7 and 8. In the dark measurement position, a vertical portion 39 of the shutter 38 completely blocks the light source 33 from the reflected light optic 34 so that a dark measurement can be taken. The dark measurement is used to compensate for imperfections in the spectrometer S.

Figure 9:
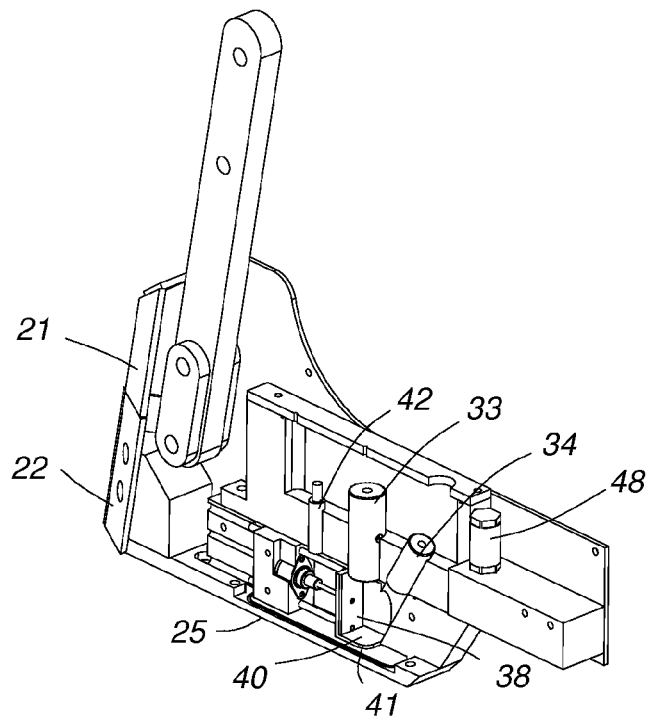
FIG. 9 is a cutaway perspective view of the reflectance module with the shutter element in an intermediate position for collecting an internal reference material measurement.
Figure 10:
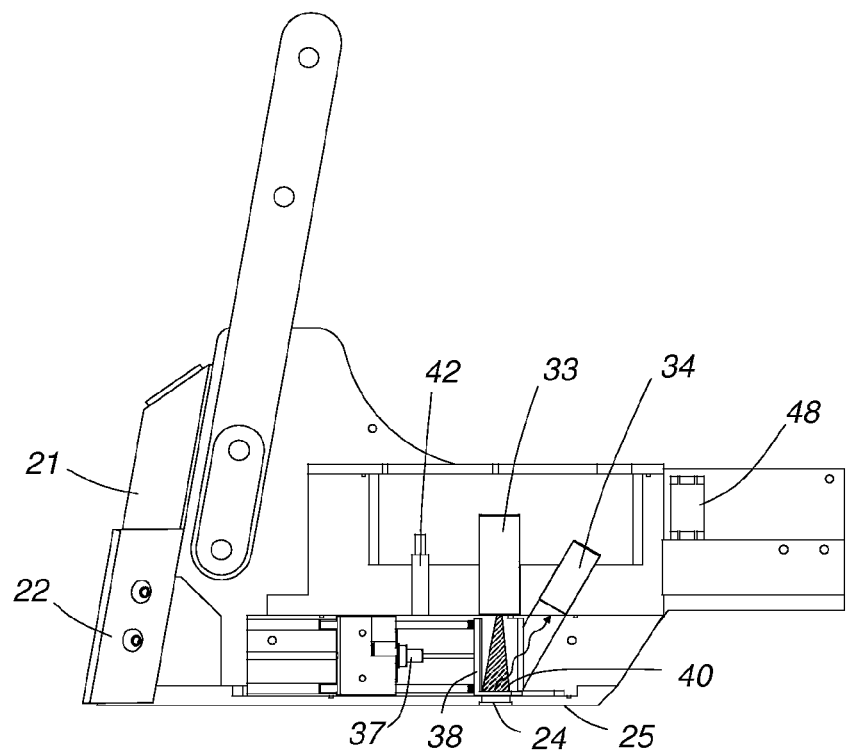
FIG. 10 is a cutaway elevation view of the reflectance module with the shutter element in its intermediate position for collecting an internal reference material measurement.

The reference measurement position of the shutter 38 is shown in FIGS. 9 and 10. In the reference measurement position, the actuator 37 moves a known reference material 40 in front of the light source 33 for reflecting light onto the optical receiver lens 34. The known reference material 40 is carried on the upper surface of a horizontal portion 41 of the shutter 38. The light from the light source 33 reflects off the known reference material 40 and into the optical receiving lens 34 to provide a light reflectance measurement for the known reference material 40. The dark and reference measurements are used to compensate for drift in the spectrometer S and the light source 33. A proximity sensor 42 relays information to the controller regarding position of the shutter 38, allowing the actuator 37 to move the shutter 38 into its proper positions.

A non-contact infrared soil temperature sensor 48 is located on the back side of the reflectance module 21. The measurement from the soil temperature sensor 48 aids in calibration because some soil reflectance characteristics change with temperature. Accounting for these changes by including soil temperature measurements in the calibration of the reflectance measurements improves results.

The slot behind the reflectance module 21 is covered by closing disks 43 that move loose soil and residue over the slot created by the opening coulter 14, shank assembly 15 and reflectance module 21, to help ensure that the soil slot does not become a channel for soil erosion.

Instrument Standardization

The NIR spectrophotometer S in the preferred embodiment is controlled by a PC-based operating system. This package covers instrument control, data-recording, and data standardization functions.

Figure 15:
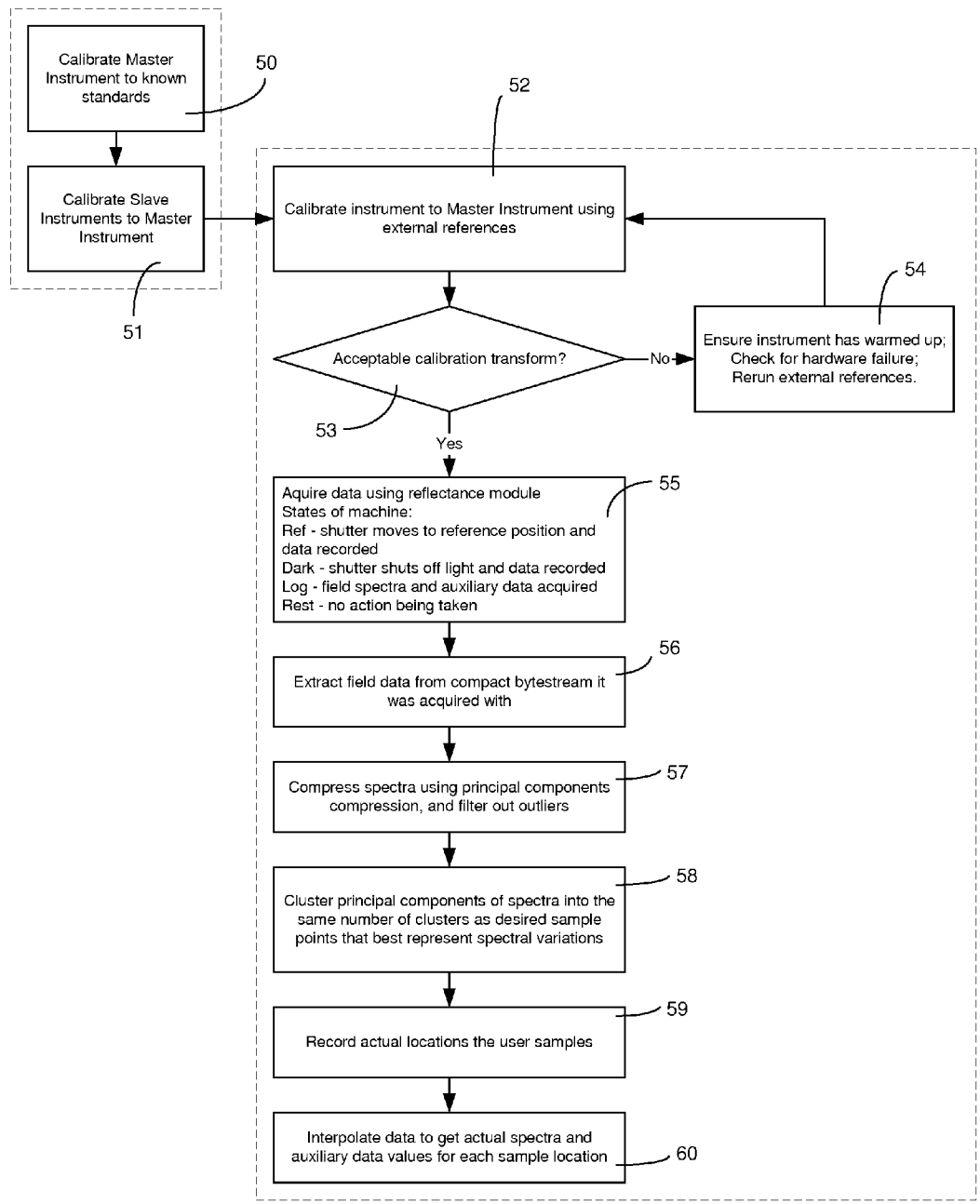
FIG. 15 is a flowchart showing the calibration and operation process used in the soil mapping system of the present invention.
Figure 16:
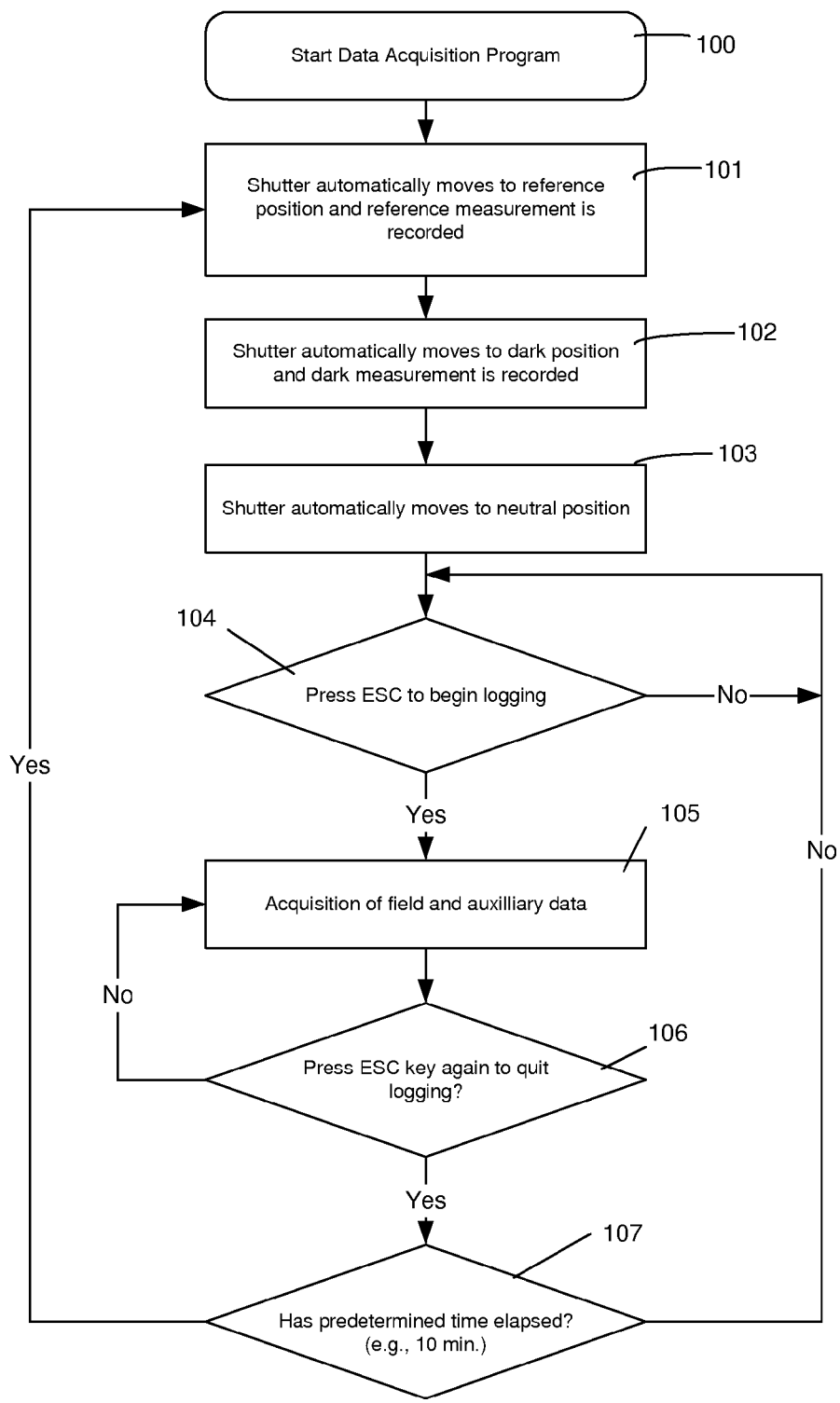
FIG. 16 is a flowchart showing the data acquisition mode of the soil mapping system.

The Applicants have developed a production and standardizing system, which is illustrated in the flowchart of FIG. 15. In this system, the NIR spectrometer unit S carried on the mobile soil mapping implement 10 is considered a slave instrument and is calibrated from a master instrument kept at the place of manufacture. The master instrument is calibrated to known reflectance standards, such as those developed by Avian Technologies, Inc., as indicated in step 50. Keeping the master instrument calibrated to known standards allows the slave (production) NIR units to be calibrated by a system traceable to these known standards. This allows the data collected from any instrument to be comparable, and compiled into soil NIR libraries—a method of leveraging local NIR measurements.

The method for calibrating the master instrument is to measure the known reflectance standards on the master instrument, and compare these measurements to the actual data provided by the standards provider. A transform is automatically created by the system software, which is applied to any data collected on the master instrument, in order to calibrate the acquired data to the reflectance standards.

Next, the slave NIR units are standardized to the master NIR unit, as indicated in step 51, by collecting four external reference measurements on the master instrument, and the same external reference measurements on the slave instrument. By gathering each of these data sets, a master transform is automatically created by the system software, which is used to calibrate the slave instrument to have the same standardized output as the master instrument. This accounts for changes in the data due to spectrometer variation.

Figure 11:
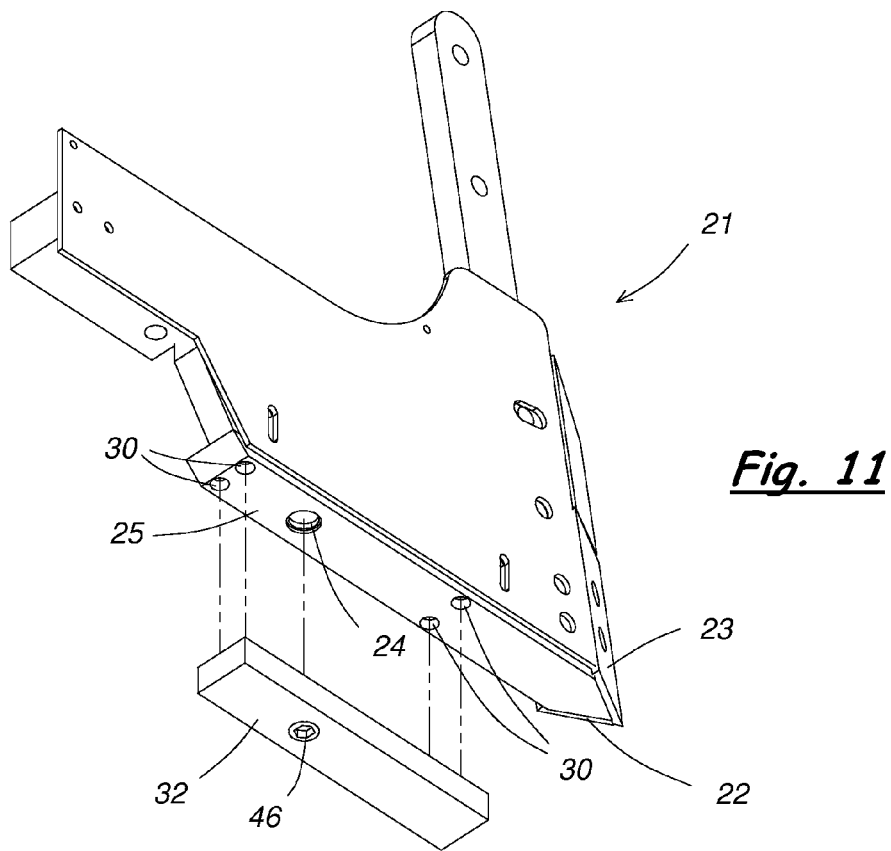
FIG. 11 is a bottom perspective view of the reflectance module with an external reference module being attached to a lower surface thereof.
Figure 12:
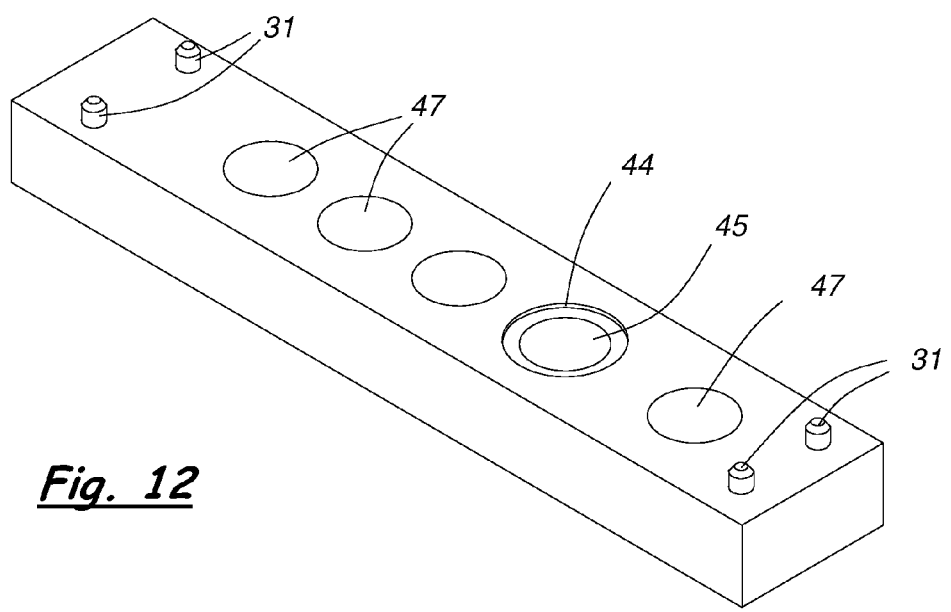
FIG. 12 is a perspective view of the external reference module.

The external reference measurements are collected from a set of four reference modules 32. As shown in FIGS. 11 and 12, each reference module 32 is made up of an aluminum block with a hole 44 cut out for a reference grayscale material. The reference material is held in place in the block 32 by a sapphire window 45 and a set screw 46. The external reference modules 32 are held in place against the wear plate 25 on the bottom of the reflectance module 21 using magnets 47 and dowel pins 31, which automatically align the reference grayscale material with the wear plate window 24 of the reflectance module 21.

Figure 13:
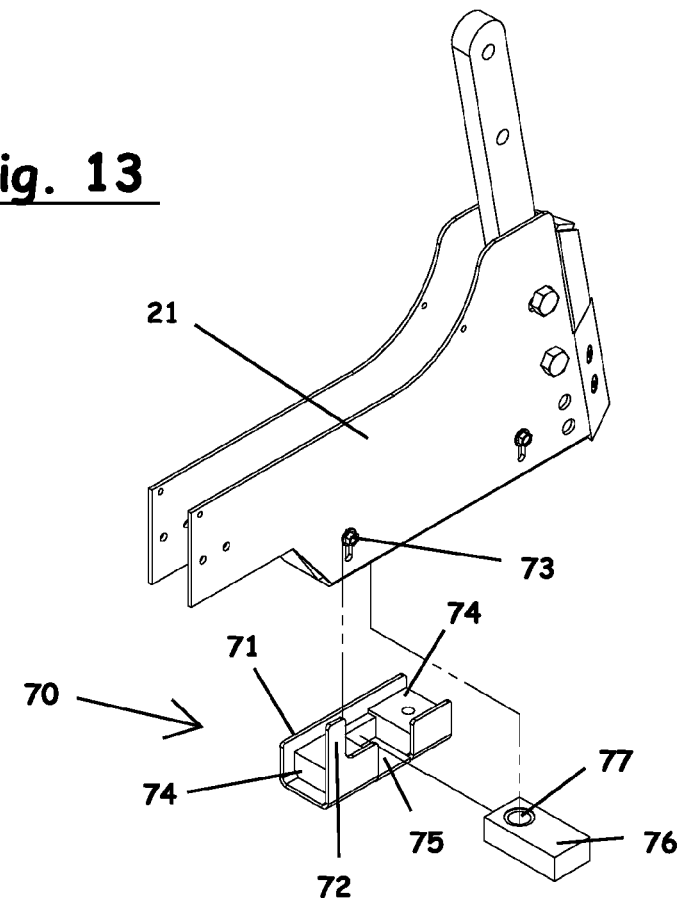
FIGS. 13 and 14 are perspective views of the reflectance module with an external reference module according to an alternative embodiment.
Figure 14:
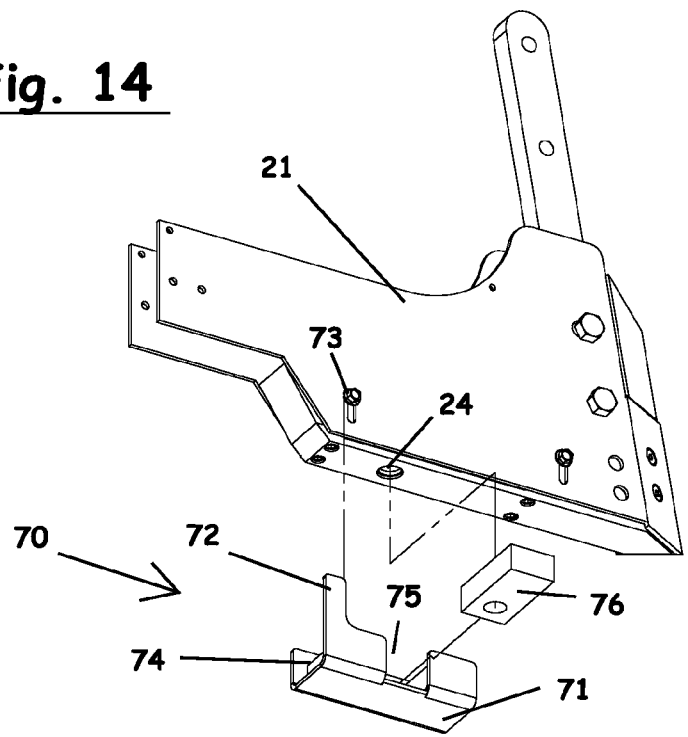

In the alternative embodiment shown in FIGS. 13 and 14, the external reference module 70 comprises a bracket 71 having a bar 72 that aligns with fasteners 73 (or bolt heads) on the reflectance module 21, magnets 74 to temporarily secure the bracket 71 to the reflectance module 21, and a cavity 75 for holding a block 76 containing the reference material aligned with the measurement window 24 on the bottom of the reflectance module 21. As in the embodiment described above, the reference material is held in place in the block 76 by a sapphire window 77. A set of four blocks 76 (only one of which is illustrated) containing different reference materials can be used one-at-a-time with the external reference module 70.

Once the slave instrument is standardized to the master by the master transform, slave instruments can be periodically calibrated back to that master transform using the four external reference modules 32, as indicated in step 52. This can be done, for example, each time before the system is used to collect data. The user places the four external reference modules 32 against the window 24, and the system check software will automatically make a system check transform to make the slave instrument calibrated back to the master for that particular time. This calibration step accounts for daily variation in the instrument.

Before advancing to data acquisition mode, the system will check to ensure that an acceptable calibration transform has been created using the external reference modules, as indicated in step 53. If an acceptable calibration transform has not been created, the operator can check to ensure that the instrument has warmed up, check for hardware failure, and rerun the external references, as indicated in step 54. Once an acceptable transform is created, the process will continue to the data acquisition mode shown in step 55.

To summarize, there are three transforms which are used to keep the slave instrument calibrated to known reflectance standards. The first is the transform used to calibrate the master instrument to the known reflectance standards. The second is the master transform given to each slave instrument to make the data comparable to data taken on the master instrument. The third is a system check transform using external references to compensate for any instrument variation due to wear or other factors that occur over time. This ensures that over time the instrument will give the same readings as it did when it was first built.

Data Acquisition

After acceptable calibration transforms are created and the system check process has been completed as described above, the system can start its data acquisition program, as indicated in step 55 of FIG. 15. The data acquisition program is illustrated in more detail in the flowchart of FIG. 16, which will now be described.

The data acquisition program starts at step 100, for example, when the user presses an "Acquisition" button on the controller. The shutter 38 in the reflectance module 21 is then automatically moved to its reference position (FIGS. 9 and 10), and a reference measurement is recorded, as indicated in step 101. The shutter 38 is then automatically moved to its dark position (FIGS. 7 and 8) and a dark measurement is recorded, as indicated in step 102. The shutter 38 then automatically moves to its neutral position (FIGS. 5 and 6), as indicated in step 103. At this point, the system is ready to begin logging soil reflectance data, and will begin when the user presses the ESC key on the laptop associated with the controller, as indicated in step 104.

Upon pressing the ESC key, the program begins acquiring soil reflectance data from the field and auxiliary data from the other sensors, as indicated in step 105. The data acquisition continues until the ESC key is pressed again, as indicated in step 106. Upon pressing the ESC key, the program determines if a predetermined time interval (e.g., 10 minutes) has elapsed, as indicated in step 107. If the time interval has elapsed, then the program will automatically return to step 101, and the system will collect another dark and reference measurement before continuing to collect additional soil reflectance data.

Data Processing

Spectral data sets can be quite large and require data compression and/or reduction in order to be used. This process is handled seamlessly in the Applicants' system software, as indicated by steps 56 to 58 in FIG. 15, after the data collection 55 is completed. The user presses one button to complete each of the following data processing steps. The first is an "extraction" step 56, in which the spectra and auxiliary data are extracted out of the compact format (bytestream) file and averaged, then the output is stored in an ASCII format. The second is a "filtering" step 57, in which the spectra are compressed using principal components compression, and outliers are removed. Maps of each principal component (up to 10) are displayed, and the results of the PC analysis and filtering are output to ASCII formatted files. The final is a "clustering" step 58 in which the principal components (PCs) of the spectra are clustered into the same number of clusters as desired sample points—suggesting sample locations (for lab-analyzed calibration samples) that best represent spectral variations.

The software then guides the operator to the suggested sample points and provides a process step 59 for recording the actual sample locations. After sampling is complete, the software provides a final processing step 60 in which the spectra are interpolated near the sample location, providing a file to be used when calibrating the spectra to the lab values for the properties of interest.

Auxiliary Electronics

While reflectance measurements are being recorded, auxiliary data and instrument data are simultaneously being recorded. An auxiliary instrument, which also controls the movements of the shutter 38 during the dark—reference routine, collects the auxiliary data. In one embodiment, the auxiliary data recorded is Electrical Conductivity Shallow (EC_SH), Electrical Conductivity Deep (EC_DP), and Soil Temperature. The instrument data recorded is the Auxiliary case temperature, Auxiliary case humidity, Spectrometer case temperature, Spectrometer case humidity, and control box temperature. The operating software monitors these and the user is alerted when any of these values are out of specification. The Spectrometer temperature is used by the operating software to control a thermal electric cooler that keeps the temperature of the spectrometer case within a set range (e.g., between 23.4-23.9 degrees Celsius). This ensures optimal data quality. To protect the spectrometer and auxiliary cases from vibration, the cases are mounted on four rubber shock absorbers. Since the spectrometer case is cooled there is foam insulation to help keep the cool air from escaping.

Unique Features

The mobile soil mapping system described above has several unique features that give it advantages over the prior art. For example, the self-cleaning window on the bottom of the reflectance module keeps mud clear, does not allow dust between the window and soil, and does not allow ambient light to interfere with the soil measurements. This proper positioning of the self-cleaning window is accomplished with down-pressure, parallel linkage, and cam angle adjustment. The window pressed against soil provides superior measurements in a wide range of soil textures and moisture conditions.

Another unique feature is the ability to collect dark and reference measurements on-the-go to compensate for spectrometer imperfections and drift of the spectrometer and the light source during operation. This feature is simplified using a single actuator and proximity sensor, and is automatic. In the preferred embodiment, the system will automatically collect a dark and reference measurement every time a predetermined time interval passes or at the occurrence of a predetermined event following the time interval. For example, the system can be set to collect a dark and reference measurement when the ESC key on the laptop controller is pressed after passage of the predetermined time interval, which normally would occur as the implement is raised to turn around at the ends of the field. Automated internal references ensure that these steps are not missed; and doing them automatically while turning keeps downtime to a minimum. The single actuator design reduces cost and complexity.

Another unique feature is the process of using external reference modules to calibrate the system at each field start-up before collecting soil data. The system will not allow data collection until an acceptable quality of measurement has been achieved. The external reference modules are magnetically-mounted to the bottom of the reflectance module, and are self-aligning so the reference material is always placed in its proper position to be scanned. The system can be made to require external reference data to be collected for calibration before the system is operational in the field.

Another unique feature is the standardization and calibration methodology that allows production NIR spectrometer units to collect matching, repeatable data. The standardization process calibrates each spectrometer to a known master spectrometer. The external reference measurements and automated internal dark and reference measurements make sure any drift or imperfection in the spectrometer and light source are accounted for and the data adjusted accordingly. Other than improper machine operation, data quality control is out of the hands of the user and quality NIR measurements are assured by the manufacturer and the operating system. Standardization allows interchangeability of spectrometers and ensures repeatable, high quality, standardized data from one system to another.

Another unique feature is the use of additional sensors to measure and collect soil data in conjunction with the soil reflectance data. In one embodiment, soil EC measurements are made simultaneously at two depths, e.g., 0-12" and 0-36". Soil temperature is also measured at the same depth as the NIR measurements. Dual-depth soil EC arrays measure soil electrical properties along with NIR simultaneously—one EC array corresponds to measurement depth of NIR, and the second EC array investigates much deeper. This combination is advantageous in that it provides a rationale for sampling areas where the shallow measurements agree, separate from areas where the deeper EC array suggests a different phenomenon is occurring. The EC electrodes can be separate from the NIR shank. Collecting soil temperature data is useful for standardizing soil property calibrations for temporal changes in soil temperature, while NIR data accomplishes a similar task for soil moisture.

The mobile soil mapping system of the present invention is a complete package for collecting soil NIR data on-the-go. From the routines that ensure calibrated, standardized data, to the implement design that maintains an ideal soil-sensor interface, to the climate-controlled cases for the instrumentation, the system is thorough but user-friendly.

Various modifications of the mobile soil mapping system of the present invention can also be made without departing from the scope of the invention. For example, additional feedback on data quality could be added, primarily related to the soil-sensor interface. Other sensors could be added to the system, including simpler and more complex electromagnetic sensors. Sensor possibilities include: light-emitting diodes (LED's), ultra-violet (UV), mid-infrared spectrometers, and gamma sensors. Electrical and electrochemical sensors could also be added, including time-domain reflectometry (TDR), capacitance, and ion-selective electrodes. The NIR measurement module could be cycled vertically every few seconds in order to collect spectra from various depths on-the-go. Soil property estimates based on previous soil calibrations could also be made on-the-go, and displayed on a computer in real-time.

While the invention has been described in connection with specific embodiments thereof, it is to be understood that this is by way of illustration and not of limitation, and the scope of the appended claims should be construed as broadly as the prior art will permit.

What is claimed is:

1. A soil mapping system, comprising:
an implement for traversing a field to be mapped; and
a reflectance module carried by the implement for collecting spectroscopic measurements of soil in the field, the reflectance module having a light source, an optical receiver for transmitting light to a spectrometer, and a shutter system for altering an optical path between the light source and the optical receiver;
said shutter system having a first position that blocks reflected light from the light source from reaching the optical receiver to provide a dark reference measurement, a second position that allows light from the light source to illuminate and reflect off a known reference material to provide a reference material measurement, and a third position that allows light to illuminate and reflect off the soil to provide soil data measurement;
wherein said reflectance module has a window located between the light source and the soil being measured, and the shutter system comprises a shutter element between the window and the light source when the shutter system is in its second position.

2. The soil mapping system according to claim 1, wherein said shutter element comprises a single shutter element movable between the first, second and third positions.

3. The soil mapping system according to claim 2, wherein the shutter element is an L-shaped member having a first portion that blocks the optical receiver when the shutter element is in its first position, and a second portion that blocks the window to the soil and places a reference material in an optical path from the light source when the shutter element is in its second position.

4. The soil mapping system according to claim 1, wherein the light source is arranged to emit light in a first direction toward the soil being measured, and the optical receiver is arranged to receive light reflected in a second direction at a predetermined angle from said first direction.

5. The soil mapping system according to claim 1, further comprising a single actuator that moves the shutter system between its first, second and third positions.

6. The soil mapping system according to claim 1, wherein the spectroscopic measurements are collected using reflectance of diffuse light in a near-infrared portion of an electromagnetic spectrum.

7. The soil mapping system according to claim 1, wherein the optical receiver is a lense that directs reflected light into a fiber optic for transmission to a spectrometer.

8. The soil mapping system according to claim 1, further comprising a proximity sensor that relays information to a controller regarding the position of the shutter system.

9. The soil mapping system according to claim 1, further comprising a controller for automatically moving the shutter system between the first, second and third positions to collect dark and reference measurements at timed intervals.

10. The soil mapping system according to claim 1, wherein said window has a lower surface arranged to maintain firm contact with the soil to prevent dust, mud and ambient light from interfering with the spectroscopic measurements.

11. A soil mapping system, comprising:
an implement for traversing a field to be mapped; and
a reflectance module carried by the implement for collecting spectroscopic measurements of soil in the field, the reflectance module having a light source, an optical receiver for transmitting light to a spectrometer, and a shutter system for altering an optical path between the light source and the optical receiver;
said shutter system having a first position that blocks reflected light from the light source from reaching the optical receiver to provide a dark reference measurement, a second position that allows light from the light source to illuminate and reflect off a known reference material to provide a reference material measurement, and a third position that allows light to illuminate and reflect off the soil to provide soil data measurement;
further comprising an external reference module and a means for aligning and removably securing the external reference module to the reflectance module to collect an external reference material measurement for calibrating the system;
wherein the external reference module comprises a block containing a known reference material aligned with and illuminated by the light source, and at least one magnet for temporarily securing the external reference module to the reflectance module.

12. A soil mapping system, comprising:
an implement for traversing a field to be mapped; and
a reflectance module carried by the implement for collecting spectroscopic measurements of soil in the field, the reflectance module having a light source, an optical receiver for transmitting light to a spectrometer, and a window located between the light source and the soil being measured;
said window having a lower surface arranged to maintain firm contact with the soil during operation to prevent dust, mud and ambient light from interfering with the spectroscopic measurements;
further comprising an external reference module and a means for aligning and removably securing the external reference module to the reflectance module to collect an external reference material measurement for calibrating the system; and
wherein the external reference module comprises a block containing a known reference material aligned with and illuminated by the light source, and at least one magnet for temporarily securing the external reference module to the reflectance module.

13. The soil mapping system according to claim 12, wherein said reflectance module comprises a wear plate on a front surface, and a bottom surface containing said window.

14. The soil mapping system according to claim 13, wherein the bottom surface of said reflectance module comprises a replaceable wear plate in which said window is mounted.

15. The soil mapping system according to claim 12, wherein said reflectance module is mounted to the implement with a parallel linkage that maintains constant down pressure on the reflectance module while allowing the reflectance module to follow undulations in terrain and maintain proper orientation to the soil.

16. The soil mapping system according to claim 15, further comprising a cam adjustment that allows the pitch of the reflectance module to be adjusted to provide adequate soil contact.

17. A soil mapping system, comprising:
an implement for traversing a field to be mapped;
a reflectance module carried by the implement for collecting spectroscopic measurements of soil in the field; and
a first external reference module for providing a first external reference material measurement for calibrating the system, said first external reference module comprising a means for aligning and temporarily securing the first external reference module to the reflectance module, and a first known reference material aligned with a measurement window on the bottom of the reflectance module, and further aligned with and illuminated by a light source;
wherein the first external reference module comprises at least one magnet for temporarily securing the first external reference module to the reflectance module.

18. The soil mapping system according to claim 17, wherein said first external reference module comprises a block having alignment projections that mate with corresponding recesses on the reflectance module, and said magnet temporarily secures the block to the reflectance module.

19. The soil mapping system according to claim 17, wherein said first external reference module comprises a bracket that aligns with the reflectance module, said at least one magnet temporarily secures the bracket to the reflectance module, and a cavity into which is placed the first known reference material aligned with the measurement window on the bottom of the reflectance module.

20. The soil mapping system according to claim 17, further comprising a second external reference module for providing a second external reference material measurement for calibrating the system, said second external reference module having a second known reference material aligned with the measurement window on the reflectance module when the second external reference module is mated with the reflectance module, said second known reference material being different from said first known reference material.

21. A method of collecting standardized soil reflectance data, comprising:
providing an implement for traversing a field to be mapped and a reflectance module carried by the implement for collecting spectroscopic measurements of soil in the field, the reflectance module having a light source and an optical receiver for transmitting light to a mobile spectrometer;
collecting a dark reference measurement and a known internal reference material measurement within the reflectance module periodically as the implement is being used; and
using the dark reference measurement and known internal reference material measurement to compensate for drift in the mobile spectrometer and light source during use;
wherein a shutter system is moved within the reflectance module between a first position that blocks reflected light from the light source from reaching the optical receiver to provide the dark reference measurement, a second position that allows light from the light source to illuminate and reflect off a known reference material to provide the known reference material measurement, and a third position that allows light to illuminate and reflect off the soil to provide soil reflectance data; and
further comprising:
creating a first transform for calibrating a master spectrometer to known reflectance standards;
creating a second transform for calibrating the mobile spectrometer to the master spectrometer;

creating a third transform for calibrating the mobile spectrometer to compensate for variation in the mobile spectrometer over time; and using the first, second and third transforms to ensure that the mobile spectrometer collects soil reflectance data calibrated to known reflectance standards.

22. The method according to claim 21, wherein a plurality of external reference blocks containing known reference materials are used to provide external reference material measurements for creating the second and third transforms for calibrating the mobile spectrometer.

23. The method according to claim 22, wherein said external reference blocks are aligned with the bottom of the reflectance module so that the known reference materials contained in the blocks are aligned with and illuminated by the light source, and at least one magnet is used to temporarily secure the external reference module to the reflectance module.

* * * * *